United States Patent [19]

de Wit et al.

[11] Patent Number: 4,465,832

[45] Date of Patent: Aug. 14, 1984

[54] MELAMINE PREPARATION

[75] Inventors: Willem de Wit, Sittard; Winfried J. W. Vermijs, Geleen, both of Netherlands

[73] Assignee: Stamicarbon B.V., Geleen, Netherlands

[21] Appl. No.: 324,389

[22] PCT Filed: Mar. 27, 1981

[86] PCT No.: PCT/NL81/00007

§ 371 Date: Nov. 16, 1981

§ 102(e) Date: Nov. 16, 1981

[87] PCT Pub. No.: WO81/02855

PCT Pub. Date: Oct. 15, 1981

[30] Foreign Application Priority Data

Mar. 29, 1980 [NL] Netherlands ................. 8001874

[51] Int. Cl.³ .......................................... C07D 251/60
[52] U.S. Cl. .................................................. 544/201
[58] Field of Search ........................................ 544/201

[56] References Cited

U.S. PATENT DOCUMENTS

| | | | |
|---|---|---|---|
| 2,566,229 | 8/1951 | Mackay | 544/201 |
| 3,014,666 | 12/1961 | Verbouwens | 239/418 |
| 3,377,350 | 4/1968 | Watson et al. | 544/201 |
| 3,475,132 | 10/1969 | Seifert | 71/58 |
| 3,727,839 | 4/1973 | Marsh | 239/8 |
| 3,831,843 | 8/1974 | Masai | 239/8 |
| 4,109,090 | 8/1978 | van Hardeveld et al. | 544/201 |
| 4,156,080 | 5/1979 | van Herdeveld | 544/201 |

FOREIGN PATENT DOCUMENTS 245261 11/1969 U.S.S.R. .

*Primary Examiner*—John M. Ford
*Attorney, Agent, or Firm*—Cushman, Darby & Cushman

[57] ABSTRACT

The invention relates to a process for the spraying of a liquid by means of a gas into a fluidized bed, in which process said spraying is conducted by means of a two-phase spraying device, consisting of a liquid feed tube fitted concentrically in a gas feed tube, in which device the end face of the liquid feed tube and the inner wall of the part of the gas feed tube extending beyond this end face are chamfered at an angle of 70°-90° so that between this face and this wall there is a conical channel, and this inner wall connects, via a rounded area, to the inner wall of an outflow channel fitted coaxially in respect of the liquid feed tube, of which channel the inside diameter is 1 to 1.6 times the inside diameter of the outflow opening of the liquid feed tube and 2.5 to 10 times the curvature radius of the rounded area.

To prevent erosion due to fluctuations in the process or to small changes in the design of the sprayer the invention is characterized in that the outflow channel, seen into the direction of flow, is conically narrowed.

3 Claims, 7 Drawing Figures

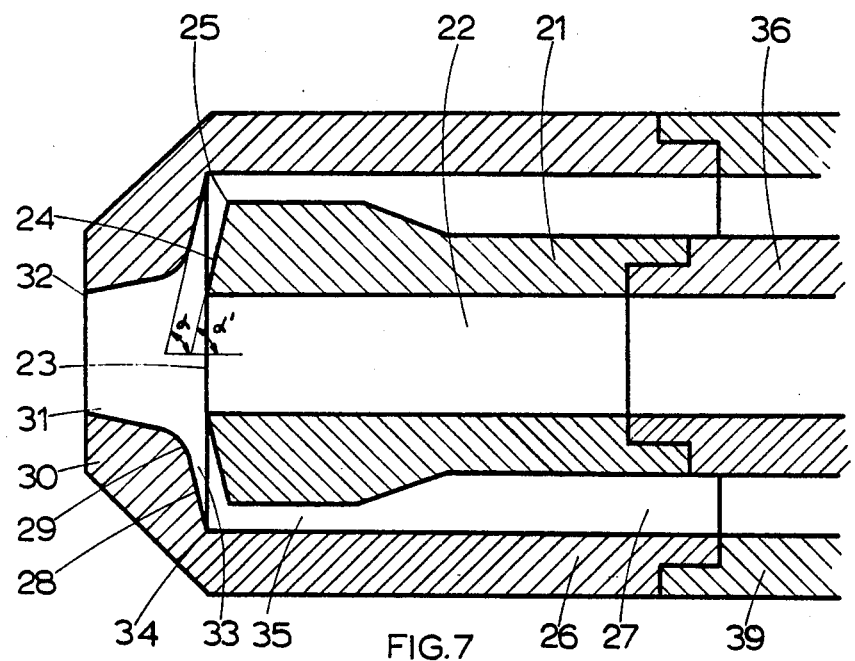

MELAMINE PREPARATION

The invention relates to a process for the spraying of a liquid by means of a gas into a fluidized bed of solid material, in which process said spraying is conducted by means of a two-phase spraying device, consisting of a liquid feed tube fitted concentrically in a gas feed tube, in which device the end face of the liquid feed tube and the inner wall of the part of the gas feed tube extending beyond this end face are chamfered at an angle of 70°–90° so that between this face and this wall there is a conical channel, and this inner wall connects, via a rounded area, to the inner wall of an outflow channel fitted coaxially in respect of the liquid feed tube, of which channel the smallest inside diameter is 1 to 1.6 times the inside diameter of the outflow opening of the liquid feed tube and 2.5 to 10 times the curvature radius of the rounded area, as known from the U.S. Pat. No. 4,109,090 (which is incorporated herein by reference).

With such a process large quantities of liquid can be sprayed at a relatively low gas velocity. This is particularly of importance in the spraying of a liquid into a fluidized bed of a solid substance, because in applying a low outflow rate there will be less pulverizing of the solid substance so that the residence time of the solid substance in the fluidized bed is increased. Furthermore, the application of low gas velocities is energetically favourable.

The known sprayers are used, inter alia, in the granulation of urea or fertilizers, such as ammonium nitrate, etc. in a fluidized bed and in the preparation of melamine by spraying urea into a fluidized bed of an inert or catalytically active material by means of ammonia or a mixture of ammonia and carbon dioxide.

A very important advantage of this sprayer compared with other known sprayers is that the outflow channel is less exposed to wear.

In certain applications of the said process, it has been found, however, that some wear of the sprayer occurs due to sensitivity of the sprayer to deviations from the optimum form.

Minor deviations from this form or changes in the operating conditions caused erosion of the outflow opening of the sprayer when used for spraying liquid into a fluidized bed of solid material.

It has surprisingly been found that the cause of this phenomenon lies in the fact that already with a small change in form or conditions, the flow picture in the outflow channel can be such that the jet issuing from the channel becomes detached from the wall of the channel. The static pressure along the wall is then lower than the pressure in the area surrounding the sprayer, in consequence of which solid substance from the fluidized bed is sucked into the outflow channel and erodes the wall in an eddy occurring at the place of the wall.

The invention provides a process for the spraying of a liquid which process is less sensitive to deviations from the optimum design or to changes in the operating conditions of the sprayers.

According to the invention the outflow channel is, seen into the flow direction, conically narrowed.

The narrowing of the channel creates a pressure increase along the wall, which increase is such that, under all circumstances, the pressure at least at the place where the medium leaves the nozzle is greater than outside the nozzle. There can then be no reflux of solid substance from the fluidized bed into the channel. However, care must be taken that the smallest diameter of the narrowed part is not smaller than the inside diameter of the outflow opening of the liquid feed tube in order to avoid wear caused by liquid flowing along the wall of the nozzle.

Generally it will suffice for only the end of the sprayer outflow channel to be provided with a narrowed part, in which case the conically narrowed part of the outflow nozzle is connected, via a cylindrical part, to the rounded transition on the inner wall of the gas feed tube. If, in this case, there should be a partial vacuum locally along the wall of the nozzle, reflux of medium from the surrounding area into the channel will yet be prevented by the pressure prevailing at the end of the channel.

The conically narrowed part of the outflow channel may consist of a ring fitted in a cylindrical channel. In that case the ring may be made of a harder material than the rest of the sprayer.

Preferably the outflow channel and the narrowed part are made in one piece.

In order to obtain the effect aimed at with the invention, it will suffice for the ratio between the smallest and the greatest diameter of the conically narrowed part to be between 0.85 and 0.95.

Preferably the vertex angle of the conical surface formed by the wall of the conically narrowed part is chosen between 5° and 90°, more specifically between 15° and 45°.

With such angles an optimum spray pattern is reached.

In the process according to the invention, such an amount of gas is preferably used that, under operating conditions, the outflow velocity of the gas is between 20 and 400 m/s and, preferably, between 40 and 120 m/s in order to prevent pulverization of the particles.

The process according to the invention is used for spraying liquid materials into a fluidized bed of solid particles, in general. The term 'liquid material' includes not only liquid solutions, e.g. water, organic solvents, aqueous solutions, compounds that have been melted or highly liquefied by heating and emulsions in aqueous or organic continuous phases, but also solid/liquid suspensions. Some examples are water, milk, waste water containing organic compounds in solution, toluene, ethyl acetate, glycerol, petroleum fractions, fuel oil and other liquid fuels, lacquers, molten urea or sulphur, molten polymers and other substances obvious to the expert.

A process of this type is of importance, inter alia, in spraying fuel or waste flows into a fluid bed incinerator or in the hydrogenation or gasification of petroleum. This process is particularly suitable for spraying molten urea into a fluid bed of inert or catalytically active material, as is usual in the preparation of melamine or cyanuric acid. In this case the atomizing gas used is ammonia or a mixture of ammonia and carbon dioxide. The temperature of the urea is at least 133° C. and in most cases between 135° and 150° C. The temperature of the gas is not critical and usually ranges between 20° and 400° C.

Furthermore, the process according to the invention is suitable for preparing granules from a solidifiable liquified material, by spraying said material into a fluidized bed of previously prepared granules. Examples of suitable material are molten urea, sulphur, ammoniumnitrate, NPK-fertilizers, calciumnitrate, etc.

The velocity with which the liquid leaves the feed tube and meets the atomizing gas may be varied within wide limits, notably between 10 and 200 cm/s and, preferably, between 50 and 150 cm/s.

The amount of gas to be used is such that the weight ratio between the gas fed in per unit time and the liquid ranges between 0.1 and 1.0, preferably between 0.2 and 0.5.

Larger amounts of gas can be used but are not necessary. The velocity with which the gas leaves the sprayer opening under operating conditions may vary within wide limits. Useful velocities range between 20 and 400 m/s, and preference is given to the use of gas velocities of between 40 and 120 m/s, more in particular of between 60 and 90 m/s.

When urea is sprayed into a fluidized bed of catalytically active particles, the gas velocity must be lower than 120 m/s and, preferably, lower than 100 m/s, to avoid pulverization of the particles.

When the process is used for preparing granules of a solidifiable liquified material, higher gas velocities, up to 400 m/s, may be apployed.

With the present process, large amounts of liquid e.g. between 500 and 4500 kg per hour, can be sprayed by means of comparatively small amounts of atomizing gas, also at gas outflow rates of, notably, less than 100 m/s. The sprayers exhibit little wear and are not readily clogged up.

The process according to the invention constitutes a distinct advance, particularly in this latter field. Although there are a great many processes that are suitable for spraying, for instance water, fuel or lacquer into a free space, there was a great need of reliable sprayers which, even at a greater capacity, could spray liquids into a fluid bed with the use of low gas velocities. The sprayers can profitably be used in fluid-bed drying installations and fluid-bed granulators, for example for granulating urea or fertilizers and for injecting fuel or waste water into fluid-bed incinerators. The sprayers are also highly suitable for spraying molten urea into a fluid bed of an inert or catalytically active material by means of ammonia or a mixture of ammonia and carbon dioxide, as is usual in the preparation of melamine on the basis of urea.

Widely diverging gases and mixtures of gases may generally be used as the atomizing gas. Examples are hydrogen, air, oxygen, lower hydrocarbons, noble gases, carbon dioxide, nitrogen, ammonia and steam. The choice of the gas depends on the substance to be sprayed and the application. If necessary, the gas may be cooled or preheated.

The invention will be elucidated with reference to the embodiments shown by way of example in the accompanying drawings. In these drawings.

Figure 3:
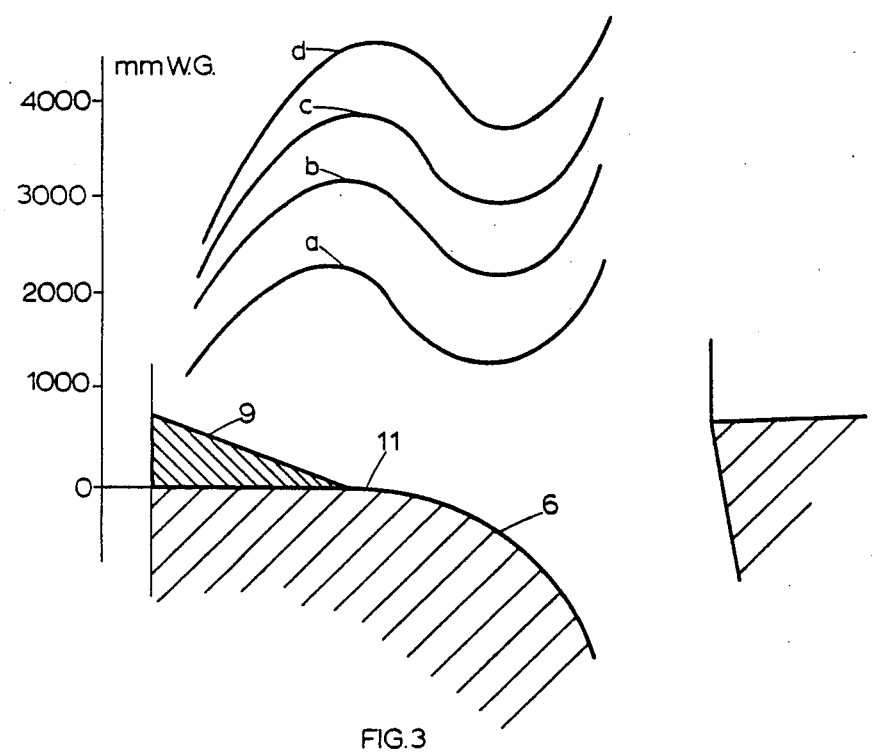

FIGS. 3 up to and including 6 show longitudinal sections of different embodiments according to the invention with the graphs going with them; and FIG. 7 is a longitudinal section of a sprayer which can be used in the process according to the invention.

Figure 1:
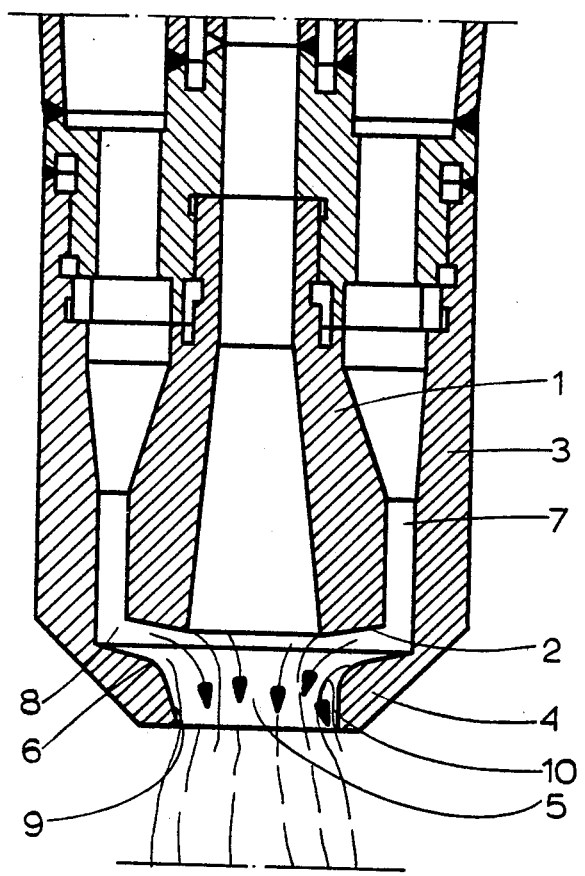
FIG. 1 is a longitudinal section of a sprayer the outflow nozzle of which is shown in its original condition on the right and after modification according to the invention on the left.

In FIG. 1 the liquid to be sprayed is supplied through a tube 1, the end face 2 of which is chamfered at an angle of 80° to the side of the sprayer. Concentrically round tube 1 a gas feed tube 3 is fitted, extending to slightly beyond the liquid feed tube and connecting to a nozzle 4, the inner wall of which also forms an angle of 80° to the centre line of the sprayer. The nozzle is provided with a central outflow opening 5, the inner wall of which connects, via a rounded area 6, to the chamfered inner wall of the nozzle. The inside diameter of tube 3 is greater than the outside diameter of tube 1 so that the gas supplied will flow out through the annular channel 7 between these tubes, the conical channel 8 between the end face 2 and the inner wall of the nozzle and the outflow opening, together with the liquid supplied, for instance into a reactor, in which process this liquid will be atomized.

In the example of the embodiment the diameter of the outflow opening of the liquid feed tube is 32 mm. The diameter of outflow opening 5 of the nozzle in the right-hand part of FIG. 1, which shows the embodiment known in the art, is 38 mm. In this design the outflow opening has a cylindrical shape. In the embodiment according to the invention shown in the left-hand part of FIG. 1 the outflow opening, seen into the direction of flow, is conically narrowed. The smallest diameter of this narrowed part 9 in the example of the embodiment is 32-36 mm. The curvature radius of the rounded area 6 is 9 mm.

In FIG. 7 the sprayer proper used in the process according to the invention consists of a feed tube 21 for liquid, which comprises an essentially cylindrical channel 22 for liquid and ends in an end-opening 23 which is normal to the direction of flow. End face 24 of tube 1 is chamfered at an angle $\alpha'$ to the axis of the sprayer. The outer boundary of that end face is preferably slightly convexly curved or radiused. Angle $\alpha'$ should be between 70° and 90°.

A tube 26 is so fitted co-axially around tube 21 that an annular channel 27 for the feed of gas is formed between the two tubes. At a zone slightly beyond the end of tube 21, tube 26 becomes narrower so as to provide at that zone an internal annular surface portion 28 at an angle $\alpha$ to the sprayer axis. That surface portion leads via a convexly curved transition 29 into a short cylindrical outflow channel 31 defined by an end portion 30 of tube 26, which outflow channel is co-axial with tube 21 and has an outlet opening 32 in a plane normal to its axis. Angle $\alpha$ should likewise be between 70° and 90°.

The end face 24 of the feed tube for liquid and the said annular surface portion 28 of the feed tube for gas define an annular channel 33 which converges towards the sprayer axis, in the flow direction, and has an apex angle or mean apex angle of between 140° and 180°.

The inner surface of gas tube 26 may be slightly concavely radiused at 34.

The term 'mean apex angle' means the mean value of the angles $2 \times \alpha$ and $2 \times \alpha'$. When angle $\alpha$ or $\alpha'$ is 70° or smaller, the capacity of the sprayer is limited whereas with an angle $\alpha$ or $\alpha'$ of 90° or more the sprayer is susceptible to extreme turbulence in the gas flow. Preference is given to the use of sprayers in which the mean value of angles $\alpha$ and $\alpha'$ is between 75° and 87.5°. Particularly good results are obtained if this mean angle is between 77.5° and 82.5°. Consequently, the 'mean apex angle' is preferably between 150° and 175° and most preferably between 155° and 165°.

Figure 2:
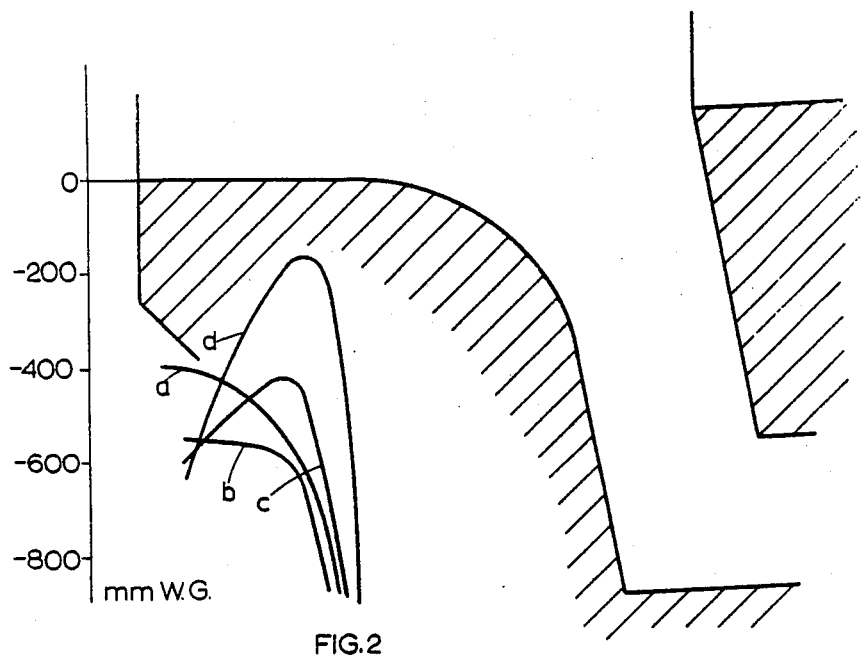
FIG. 2 shows a longitudinal section of the wall of the outflow nozzle in its original condition with a graph showing the pressure occurring along the wall under different loads.

It is favourable so to choose the angles $\alpha$ and $\alpha'$ that $\alpha$ is greater than $\alpha'$ and that the differences between these angles is less than 5°. Special preference is given to the embodiments in which $\alpha$ and $\alpha'$ are equal or substantially so, so that the converging annular channel 33 has substantially parallel walls. This means that in preferred embodiments of sprayers according to the invention, the annular channel along which the gas flow moves towards the sprayer axis has substantially parallel walls and has an apex angle of between 150° and 175° and, most preferably of between 155° and 165°.

In these preferred embodiments comparatively little gas is required for efficient atomization, and the chance of turbulence forming in the gas flow and in the outflow opening of the sprayer is particularly small. This is particularly important in sprayers used for spraying a liquid into a fluidized bed of solid particles.

Liquid feed tube 21 is connected as known in the art, e.g. by a welded or bolted connection, to liquid feed tube 36, which, in the embodiment shown, is provided with a welded outer jacket 37, so that a space 38 is formed which may be filled with heat-insulating material of may be made suitable for the circulation of a heat-transfer agent or for an electric heating system. This tube 36 is connected to a device for the supply of liquid by means of conduits in a way not shown in the drawing.

Tube 26 is connected as known in the art to a tube 39 connected to a device for the supply of gas in a way not shown in the drawing.

In the sprayer according to FIG. 7, the liquid feed tube has a thicker end part and the gas passageway 27 leads into a portion 35 having a smaller cross-sectional area.

Outflow channel 31 is comparatively short; in most cases the end portion 30 of the gas tube has a length of only between 1/5 and ½ the diameter of outflow opening 32. If the outflow channel is longer, there is a risk of the wall of tube portion 30 being wetted with liquid. The spraying of certain liquids, e.g. molten urea or salt solutions, might give rise to corrosion. In any case the diameter of the outflow opening of the sprayer is taken to be the smallest diameter of channel 31.

If so desired, tube 21 may be so shaped that liquid channel 22 slightly converges or diverges towards its end opening 23, but the occurrence of turbulence in the liquid flow must be avoided.

The diameter of the outflow opening 32 of the sprayer is from 1.0 to 1.6 times, and preferably between 1.1 and 1.3 times, the diameter of end opening 23 of the feed tube for liquid.

If the sprayer outflow opening is too small, the wall of the outflow channel is wetted by liquid, and if the opening is too large, the atomization is poor, or too large amounts of gas or too high gas velocities are needed for the atomization.

The distance between surface portions 24 and 28, defining converging channel 33 must be such that the area available for the passage of gas is equal to or greater than the area of the sprayer outflow opening. Hence, when the gas passes through channel 33 and channel 31 to outflow opening 32, it must have an unchanging or increasing velocity. The velocity preferably increases, and hence the passage area in channel 33 is preferably greater than the passage area of the sprayer outflow opening.

The passage area of the converging channel 33 is taken to be generally the passage area in the part of the channel nearest to the sprayer outflow opening. If so desired, the gas velocity in the sprayer outflow could be lower than the gas velocity in the said converging channel, but then the chance of turbulence being formed near the sprayer opening and in the outflow channel, with consequent erosion, increases.

As the sprayer is intended for spraying liquid into a fluidized bed of catalytically active or inert particles, it is to be recommended partly to round or to chamfer the end of the sprayer (the end face of gas tube portion 30) to reduce wear and to promote suction of the catalyst particles, so that catalyst and liquid are mixed better.

Rounding of surface portion 29 between annular surface portion 28 and outflow channel 31 is of essential importance. If the radius of curvature of portion 29 is too small, or if there is no rounding, increased wear occurs by liquid drops of solid particles being drawn onto and into the sprayer head. If the radius of rounding is too great, too much gas or too high a gas velocity is needed to effect proper atomization. The radius of rounding of part 29 must be chosen to counter formation of turbulence in the gas flow. This is achieved by choosing a radius of curvature from 0.1 to 0.4 times the diameter of the outflow opening of the sprayer, preferably between 0.125 and 0.375, and most preferably between 0.2 and 0.3, times such diameter. By preference, the outer boundary at 5 of the end face of the liquid feed tube is also slightly rounded to prevent turbulence in the gas flow. If this boundary is not rounded, some turbulence may occur, causing settlement of liquid on the end face of the tube. As a result, corrosion might occur in some cases. As a further measure to prevent turbulence, joint 34 is preferably also rounded slightly. At these two places the radius of rounding is not critical.

With due observance of the essential ratios referred to above, the dimensions of the sprayer are determined by the desired capacity of the sprayer.

A capacity of over 4000 kg of liquid/hour can be reached without further measures. For spraying corrosive media, the structural material for the sprayer may be any material that is non-corrosive, dimensionally stable and wear-resistant under the operating conditions. Suitable materials are, inter alia, Inconel, Hastalloy B or Hastalloy C. The parts of the sprayer that are most subject to wear, such as parts 28, 29, and 30, may be lined with a layer of wear-resistant material or may be formed by inserts of highly resistant material, such as silicon carbide, tungsten carbide or alumina.

The process according to the invention is particularly suitable for use in the preparation of melamine, when, by means of a two-phase sprayer, urea is sprayed into a fluidized bed of catalytically active or inactive material in a reactor in which a pressure of between 1 and 25 atmospheres and a temperature of between 300° and 500° C. are maintained and which contains one or more fluidized beds, at least one of which consists of catalytically active material. The synthesis of melamine from urea in this way is known in itself, for example from the U.S. Pat. No. 4,156,080.

In the known embodiment, when in operation, there will be a partial vacuum at the inner wall of the outflow opening, in consequence of which medium and solid substance from the surroundings of the sprayer will be sucked into the sprayer. Owing to the solid substance sucked in, there will be erosion of the wall of the sprayer outflow channel. In the embodiment according to the invention this does not happen, as will be explained hereinafter.

In a number of experiments different sprayers were examined using water as liquid to be atomized and air as atomizing gas. In all experiments the quantity of air was 550 m³/h and the quantity of water 0-500-1000 and 2000 l/h. In these experiments a thin measuring probe was used to determine the pressure at different places along the wall of the outflow opening. The graphs in FIGS. 2 up to and including 6 give the difference between this pressure and the pressure in the surrounding area. In these graphs, line a shows the pressure variation along the wall at a load of exclusively 550 m³ of air/hour. Lines b, respectively c and d, show this pressure variation if, in addition to this air, 500, respectively 1000 and 2000, litres of water/hour are supplied.

EXAMPLE I (COMPARATIVE EXAMPLE)

A sprayer with a cylindrical outflow opening (diameter 38 mm) was examined. These experiments show that, under all circumstances, the pressure along the wall is lower than the pressure outside the nozzle. Depending on the place and the gas/liquid load, pressure differences with respect to the immediately surrounding area of −400 mm WG to more than −1000 mm WG were measured (−3.9 kPa to −9.8 kPa). It has been found in practice that this sprayer is subject to wear.

EXAMPLE II

In the outflow opening of the nozzle a conical insert ring 9 is fitted. The smallest diameter of this ring equals the diameter of the outflow opening of the liquid feed tube and is 32 mm, while the vertex angle of the conical surface formed by the wall of the conically narrowed part is 41°. As shown in the graph of FIG. 3, the static pressure along the wall over the full length of the outflow channel is, at all loads, higher than the pressure of the surrounding area so that, when applying this design, no wear is expected in practice.

EXAMPLE III

Figure 4:
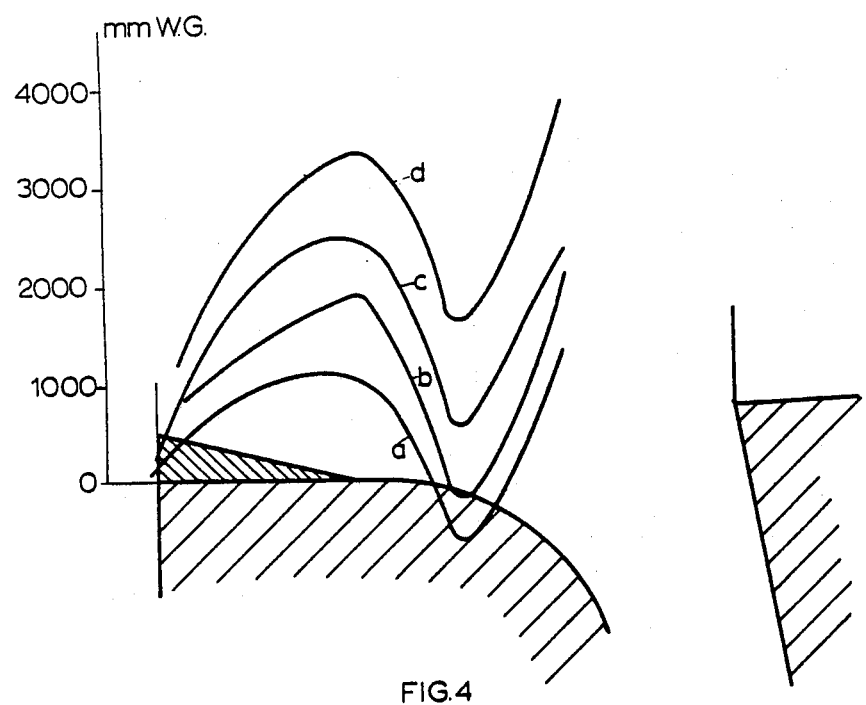

This embodiment corresponds with that of example II with this difference that the smallest diameter of the insert ring is now 34 mm and the vertex angle 28°. The graph in FIG. 4 shows that, reckoned from the end of the sprayer outlet channel, the static pressure over a certain length along the wall is higher and locally further on lower than the pressure of the surrounding area. This low-pressure area is isolated, however, from the surrounding area by the higher pressure at the end of the sprayer nozzle, so that there can be no reflux of medium from the surrounding area into the nozzle. In experiments with a load of 1000, resp. 2000 l of water/h the static pressure over the full length of the wall was higher than the pressure of the surrounding area. When used in practice, this sprayer will not be exposed to erosive wear either. This sprayer has the advantage, compared with the embodiment according to FIG. 3, that the flow resistance is smaller.

EXAMPLE IV

This embodiment corresponds with those of examples II and III with this difference that the smallest diameter of the insert ring is now 36 mm and the vertex angle 14°. The static pressure over a certain length along the wall reckoned from the end of the outlet channel, is higher, and at some places further on, lower (about 1500 mm WG, resp. 14.7 kPa) than the pressure of the surrounding area round the sprayer. The low-pressure area is then again isolated from the surrounding area by the higher pressure at the end of the sprayer nozzle.

Figure 5:
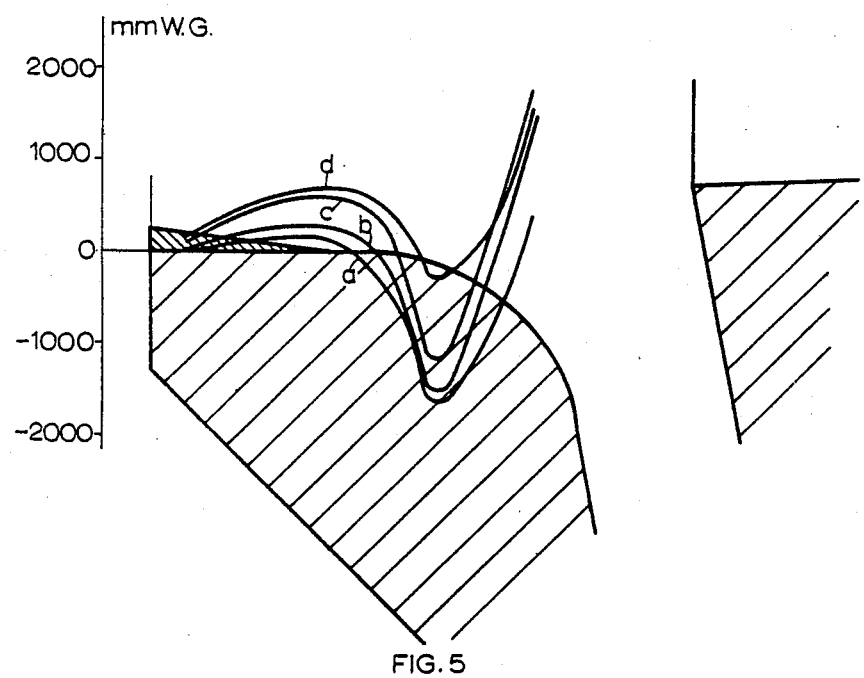

In the embodiments according to FIGS. 3–5 the conically narrowed part is of such a length that, between this narrowed part and the rounded area 6, there is yet a cylindrical part 11. In the embodiment according to FIG. 6 there is a flowing transition from the rounding area to the conically narrowed part.

EXAMPLE V

Figure 6:
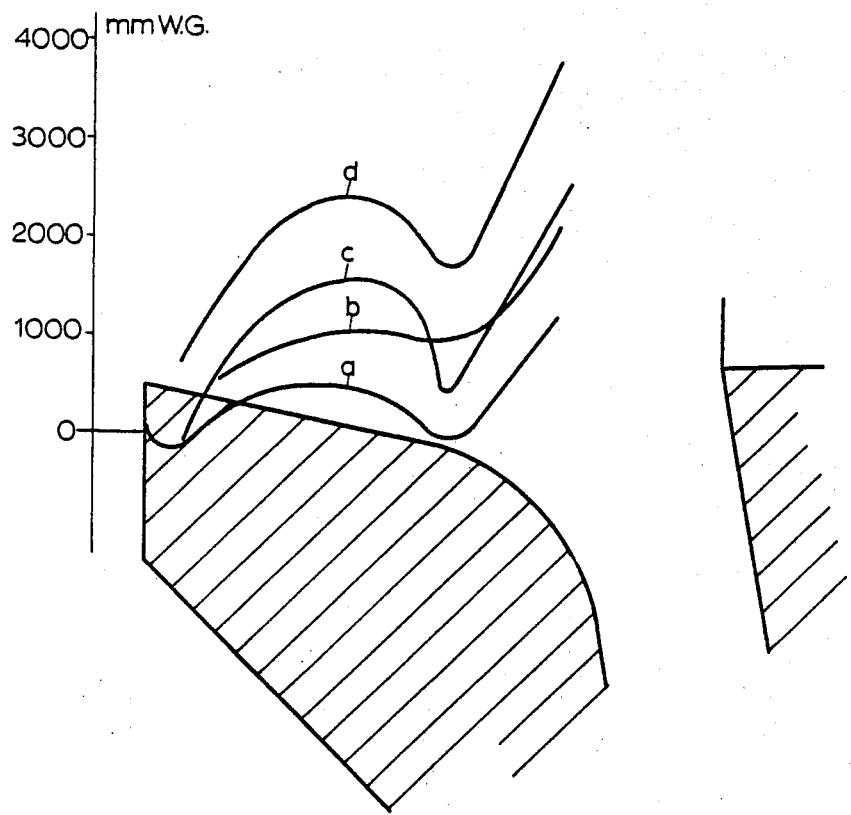

A sprayer was examined in which the narrowed part in the nozzle was connected, in a flowing line, to the rounded area of the conical channel and in which the smallest diameter of the narrowed part was 34 mm. The measuring results given in the graph of FIG. 6 show that, if only gas load is applied, the static pressure along the wall is lower (−100 mm WG, resp. −1.0 kPa) over the first 2 mm, reckoned from the end of the sprayer outlet channel, and further on, over the full length, higher than the pressure of the surrounding area round the sprayer. At a load with liquid and gas the pressure over the full length of the outlet channel is higher than the surrounding pressure. Therefore, with this sprayer, when used in practice, no erosive wear is to be expected.

EXAMPLE VI

The sprayer described in Example V was used for spraying molten urea at about 135° C. directly into a fluidized bed of catalytically active material in a melamine reactor with ammonia as the atomizing gas. Under operating conditions the outflow velocity of the ammonia gas was 80 m/s, while the urea load was varied between 1000 kg of urea/hour and 3600 kg/hour. The reactor and the sprayer were inspected after the sprayer had been operating virtually continuously for 18 months, mostly at a load of about 2000 kg of urea/hour.

The sprayer did not show any serious signs of erosion. No pronounced signs of corrosion, such as pitting, were observed, neither in the reactor itself, nor in the heat exchangers fitted in the reactor. From this it may be concluded that the sprayer always operated properly in this period. Indeed, if the atomization is poor, drops of urea will hit the reactor wall and the heat exchanger when this type of sprayer is used, so that serious signs of corrosion will occur soon.

The invention is not limited to the numbers given by way of example in the examples of the embodiments. Depending on the capacity of the device in which the sprayer is applied, an adjustment of the diameters of the various parts will have to be effected.

We claim:

1. In a process for preparing melamine wherein molten urea is atomized and sprayed by means of an atomizing gas selected from the group consisting of ammonia or a mixture of ammonia and carbon dioxide through a two-phase sprayer into a fluidized bed of a particulate solid catalytically active material wherein said sprayer is comprised of a liquid feed tube adapted for the supply of molten urea, terminating with a liquid outflow opening and positioned around the axis of the sprayer and coaxially within a gas feed tube adapted for the supply of atomizing gas and terminating with a sprayer outflow opening, said liquid and gas feed tubes being relatively positioned such that said gas feed tube extends beyond the liquid outflow opening of said liquid feed tube, and wherein, in said sprayer, said gas feed tube near the sprayer outflow opening has an inner wall section that tapers narrower towards the sprayer outflow opening at an angle α of between 70° and 90° with respect to the sprayer axis, and continues by way of a rounded shoulder into an outflow channel ending at said sprayer outflow opening, the smallest diameter of said outflow channel being 2.5 to 10 times the radius of said rounded shoulder, and between 1.0 and 1.6 times the diameter of said liquid outflow opening, and said liquid feed tube has an outer wall, and an end face between said outer wall and liquid outflow opening chamfered at an angle $\alpha'$ of between 70° and 90° with respect to the sprayer axis thereby forming a conical channel with an average apex of between 140° and 180° between said chamfered end face and the tapered inner wall section of the gas feed tube, the improvement wherein at least a portion of said outflow channel is conically narrowed in a direction such that the diameter of the sprayer outflow opening is less than the diameter of any other portion of said outflow channel.

2. The process of claim 1 wherein the ratio between the smallest and the greatest diameter of the conically narrowed part of the outflow channel is between 0.85 and 0.95.

3. The process of claim 1 or 2 wherein the vertex angle of the conical angle formed by the wall of the conically narrowed part is between 5° and 90°.

* * * * *